(12) United States Patent
Gerten

(10) Patent No.: US 10,213,338 B2
(45) Date of Patent: Feb. 26, 2019

(54) DEVICE FOR PRODUCING CUTS OR PERFORATIONS ON AN EYE

(71) Applicant: VOSSAMED GMBH & CO. KG, Köln (DE)

(72) Inventor: Georg Gerten, Bonn (DE)

(73) Assignee: VOSSAMED GMBH & CO. KG, Köln (DE)

( * ) Notice: Subject to any disclaimer, the term of this patent is extended or adjusted under 35 U.S.C. 154(b) by 188 days.

(21) Appl. No.: 15/305,784

(22) PCT Filed: Apr. 27, 2015

(86) PCT No.: PCT/IB2015/053047
§ 371 (c)(1),
(2) Date: Oct. 21, 2016

(87) PCT Pub. No.: WO2015/166394
PCT Pub. Date: Nov. 5, 2015

(65) Prior Publication Data
US 2017/0042734 A1 Feb. 16, 2017

(30) Foreign Application Priority Data

Apr. 28, 2014 (DE) .......................... 10 2014 105 943

(51) Int. Cl.
*A61F 9/007* (2006.01)
(52) U.S. Cl.
CPC ................. *A61F 9/00754* (2013.01)
(58) Field of Classification Search
CPC .................................................. A61F 9/00754
See application file for complete search history.

(56) References Cited

U.S. PATENT DOCUMENTS

| 5,269,787 | A | 12/1993 | Cozean, Jr. |
| 9,254,224 | B2 | 2/2016 | Keller |
| 2003/0014066 | A1* | 1/2003 | Hall ............... A61B 17/320758 606/167 |

(Continued)

FOREIGN PATENT DOCUMENTS

| DE | 4012882 A1 | 10/1991 |
| DE | 10220253 A1 | 11/2002 |

(Continued)

OTHER PUBLICATIONS

International Search Report of PCT/IB2015/053047 dated Aug. 3, 2015.

(Continued)

*Primary Examiner* — Richard Louis
(74) *Attorney, Agent, or Firm* — Rankin, Hill & Clark LLP

(57) ABSTRACT

A Device for producing cuts or perforations on a human or animal eye at the anterior or posterior opening of the eye lens (capsulatomy, rhexis) with a cutting element that can be inserted into the interior of the eye and a drive device which is arranged outside of the eye in order to cause movement, in particular oscillatory vibrations or rotation of the cutting element inside the interior of the eye, the drive device having a field generator for generating a magnetic or electromagnetic excitation field and the cutting element can be excited, in particular driven, by way of the excitation field generated by the field generator.

5 Claims, 5 Drawing Sheets

(56) References Cited

U.S. PATENT DOCUMENTS

| | | | |
|---|---|---|---|
| 2003/0088254 A1* | 5/2003 | Gregory, Jr. .........  | A61B 17/221 606/127 |
| 2004/0092982 A1 | 5/2004 | Sheffer | |
| 2010/0241130 A1 | 9/2010 | Deli | |
| 2010/0312252 A1 | 12/2010 | Jia | |
| 2012/0158027 A1 | 6/2012 | Moradian | |
| 2012/0158130 A1 | 6/2012 | Moradian | |

FOREIGN PATENT DOCUMENTS

| | | |
|---|---|---|
| WO | 198503217 A1 | 8/1985 |
| WO | 2012122325 A2 | 9/2012 |

OTHER PUBLICATIONS

Espacenet bibliographic data for DE Publication No. 4012882 published Oct. 31, 1991, 1 page.

Espacenet bibliographic data for DE Publication No. 10220253 published Nov. 14, 2002, 1 page.

Espacenet bibliographic data for WO Publication No. 8503217 published Aug. 1, 1985, 1 page.

Espacenet bibliographic data for WO Publication No. 2012122325 published Sep. 13, 2012, 1 page.

* cited by examiner

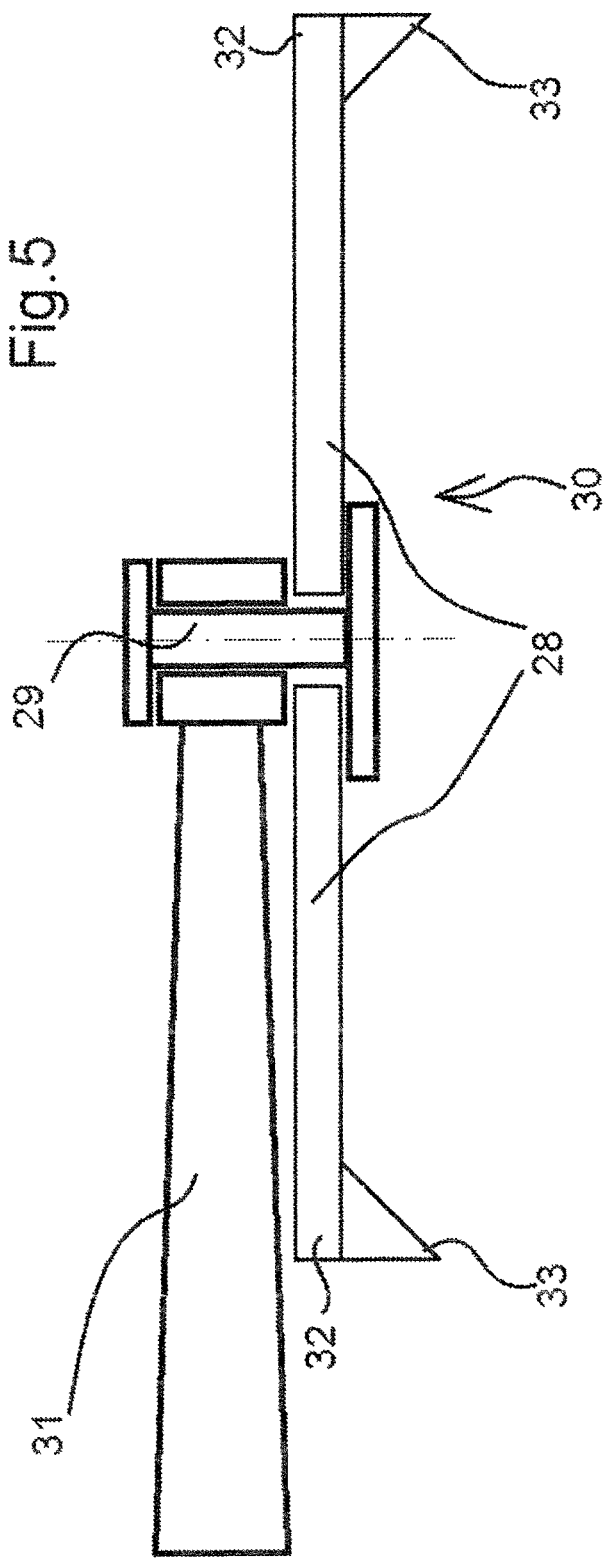

DEVICE FOR PRODUCING CUTS OR PERFORATIONS ON AN EYE

The invention refers to a device for producing cuts or perforations on a human or animal eye at the anterior or posterior opening of the eye lens (capsulatomy, rhexis) with a cutting element that can be inserted into the interior of the eye and a drive device which is arranged outside of the eye in order to cause movement, in particular oscillatory vibrations or rotation of the cutting element inside the interior of the eye. The device according to the invention is therefore particularly suitable for use in ophthalmic surgery, especially for cutting out parts of the capsule of the human eye lens.

BACKGROUND OF THE INVENTION

Operations on the human or animal eye lens belong to the operations most frequently carried out worldwide. Such operations become necessary as a result of pathological processes which mostly affect the interior of the eye lens, such as clouding of the eye lens (cataract formation) and/or hardening of the lens nucleus in presbyopia or if a change in the refractive power of the lens/eye is to be achieved. With modern surgical methods the interior of the eye lens (nucleus, epithelium) is removed, normally by opening the lens capsule sac only at the anterior face and otherwise leaving it alone. However, in some cases the capsule sac is intentionally opened at both the anterior and posterior faces.

The empty capsule sac remaining after removal of the interior of the natural eye lens is then generally used to accommodate an artificial intraocular lens (IOL) which replaces the removed interior of the eye lens and restores the vision of the patient, taking into account the desired optical correction of the eye. The centered alignment, shape, size and stability/integrity of the anterior opening of the capsule sac (capsulorhexis and/or rhexis) assume particular importance here. The rhexis is one of the factors which is decisive for the result of the entire operation. Its stability/integrity is important for the progress of the operation itself. The aim is to achieved a round rhexis without ridged edges, tears or inhomogeneities, as this will form a stable hole in the capsule sac. As a result, the capsule sack does not tear during the operation despite manipulations inside the lens interior. If this stability/integrity of the rhexis is not ensured, tears can arise in the capsule sac which can result in complications during the operation (e.g. loss of lens material into the vitreous humour space, difficulty to impossibility of implanting an artificial intraocular lens IOL, prolapse of the vitreous humour, etc.). Centered alignment, shape and size of the rhexis are also important for the post-operative result. This is because the capsule sac experiences a postoperative shrinking process, which can vary greatly between individuals. Lens epithelium cells remaining in the capsule sac can migrate, divide and agglomerate. The so-called "secondary cataract" can lead to distortion of the capsule sac and clouding of the remaining parts of the capsule. The posterior lens membrane can become grown over with epithelium cells, become cloudy and severely impair the vision. A central hole must then be cut behind the implanted intraocular lens (IOL) in the posterior capsule membrane, usually with an Nd YaG laser, to clear the optical axis again. The surgeon usually tries to keep the size of the rhexis during lens operations to between 4 and 5.5 mm. Too small a rhexis can lead to subsequent complications (capsular phimosis) in just the same way as too large a rhexis compared to the IOL (OIL lens becoming caught in the rhexis, and off-centerdness of the IOL). A rhexis which is off-center from the IOL, which does not cover the front of the IOL in a circular manner, can lead to pressure by the shrinking rhexis edge on the IOL lens and to the IOL being off-center. The same applies if the shape of the rhexis is not round.

In addition to the rhexis described above, which should usually be as a round a hole as possible centered in the front of the capsule sac (other more oval forms of the rhexis may also be appropriate in certain situations), a posterior rhexis is also created in some cases. This is also a circular hole, in the posterior face of the lens capsule. The same considerations apply in principle for a posterior rhexis as for an anterior rhexis. A posterior rhexis is technically more difficult to accomplish, however, and more risky from a medical aspect. The anterior part of the vitreous body is in direct contact with the posterior capsule and the anterior vitreous membrane should not be injured by a posterior rhexis.

Previous methods of opening the eye lens capsule have been based on mechanical procedures or optical methods, in other words laser surgical methods, particularly involving the use of a femtosecond laser. The simplest mechanical methods are carried out purely mechanically. These entail introducing a needle or forceps into the anterior chamber of the eye. This then perforates the anterior capsule and a more or less round, centered hole of approx. 5 mm diameter is made in the anterior capsule (rhexis or capsulotomy). The centered alignment, shape, size and stability/integrity of the capsular rhexis produced in this manner depend greatly on the skill of the surgeon and the conditions in each individual case. The manual methods can also be assisted by devices such as the Fugo Blade® or Cystotome®. However, these methods still have the disadvantage, among others, that all they can do is produce a point-shaped perforation at a particular place. The surgeon still then has to create the complete, usually circular, cut in the capsule by hand by guiding the device over the capsule in as circular a motion as possible of the required diameter.

Devices are also known that use thermal/electrical effects to cut the capsule open (WO 2010/141181 A1). This has the disadvantage of introducing electric current into the eye and also heating up the ocular tissue.

Optical cutting/perforating of the lens capsule using ultra-short pulse laser systems is already in clinical use. This makes use of the interaction with tissue of ultra-short pulse lasers. The perforation is created by non-linear effects of the ionisation/plasma formation in the ocular tissue at extremely high photon densities. The expansion of the cavitation bubble this causes finally tears the tissue locally. Clinically, postoperative perforation of the anterior capsule as secondary cataract treatment is usually done with Nd YaG lasers, which emit infra-red laser pulses in the nano- or picosecond range with J of energy, One new development is the use of femtosecond lasers for capsulotomy during the operation. These lasers emit radiation mostly in the near-infra-red or ultraviolet range. Pulses from a few fs to several hundred fs are emitted. This allows successful precise cutting of the ocular tissue with a considerably smaller energy input (individual pulses are in the µJ range). The capsulotomies that can be achieved this way are very stable, centered and circular. However, the patient's eye has to be firmly connected to such a laser device for this. The patient has to be placed under the laser device and the patient's eye held by suction. This prolongs the operation time and procedure. In addition, the devices are very large, demand considerable maintenance, and are expensive. However, clinical trials have confirmed the considerable value of a centered, round and integral rhexis as can be produced with a femtosecond laser.

The capsule exhibits considerable elasticity (E modulus is approx. 1.3 N/mm$^2$). This has to be taken into account during mechanical perforation/cutting of the capsule. Cutting heads, among other things, are therefore described that attach to the capsule by suction during the cutting process (WO 2009/140414 AI). These have a number of disadvantages: Attaching to the lens capsule by suction within the eye is not without risks, since the liquid reservoir in the anterior chamber of the eye is limited and the anterior chamber can therefore collapse, thereby damaging the ocular tissue. This is particularly likely because the suction device in the eye has to operate with the corresponding vacuum, and must therefore be quite large and non-portable.

A medical instrument for use in cataract surgery and a method to be carried out with it are known from US 2004/0092982 A1, in which a cutting element in the form of a cutting ring that can be inserted into the interior of the eye is arranged on a handle that remains outside the eye, the handle being connected to a flexible shaft by means of which a rotary motion from an external motor is introduced into the instrument to drive the cutting ring. The instrument is relatively bulky and not easy for the surgeon to handle.

U.S. Pat. No. 5,269,787 discloses a cutting ring arranged on a shaft to produce an opening in the anterior capsule of the human eye, in which the shaft is connected to an ultrasound source in order to impart vibrations to the cutting ring and thereby perforate the anterior capsule.

Both known instruments share a common feature in that they need to be held and manipulated by the surgeon on the handle or shaft respectively during the cutting process, which means that every incorrect manipulation inevitably affects the cut to be made. With these devices, the kinetic energy to perform the cut is transmitted to the cutting ring by having the said cutting ring mechanically coupled to the drive, which necessitates various components such as couplings, flexible shafts and the like. This has the disadvantage that the drive energy for cutting element has to be transmitted into the eye by means of moving parts, i.e. the drive and cutting element are joined together mechanically. This means that rotating moving parts, which therefore give off heat, must be introduced into the eye through a cut.

All of the patents and patent applications referenced herein (and any English equivalences thereof) are hereby incorporated by reference for showing the same and form part of the specification of this application.

SUMMARY OF THE INVENTION

It is an object of the invention to create a device for perforating and/or cutting tissue, particular at the eye, so that a clean cut of the right shape can be made at the right position.

This task is solved by the invention by incorporating a field generator in the drive device to produce a magnetic or electro-magnetic induced field and having the cutting element capable of excitation by the induced field generated by the field generator and therefore capable of being driven without a mechanical coupling. Advantageous further developments of the invention are the object of the dependent claims.

In the invention, the cutting element is driven by a magnetic field generated by coils of the field generator located outside the eye. The cutting element itself contains ferromagnetic parts and can therefore be excited by the (electro)magnetic field. The cutting element, which is preferably designed as a cutting ring, can therefore be caused to carry out a rotation or part of a rotation or a circumferential oscillatory motion when inside the interior of the eye.

It is possible for the cutting element—unlike known instruments—to have no mechanical connection to a handle held by the surgeon or the like, and in addition to being merely set into rotational or oscillatory motion by means of the (electro)magnetic field generated by the field generator, is also held in its desired position in the eye where the surgeon has previously brought it. This means that not only can the cutting element be held in the desired centered position with the field generator, but it is also possible to exert force on the cutting element in the axial direction, to that it is held pressed against the capsule to be cut, and consequently the cut is effected around the entire circumference in a particularly easy and reliable manner.

One embodiment in which the cutting element mounted on a bearing in a holding element such that is free to move, in particular to rotate, and with which it can be introduced into the interior of the eye through an opening, has proved to be especially advantageous. With the aid of the holding element, the surgeon, after he has opened up the anterior chamber of the eye with a small cut or hole, can introduce the cutting element, which is mounted in bearing at the remote, free end of the holding element, into the eye and hold it in the desired position while the (rotary) drive of the cutting element then takes place without any contact by switching on the magnetic field generated by the field generator. The holding element can of course also be manipulated for this purpose by a robot provided for this purpose that can handle the tool with high precision and hold it reliably in the found desired position.

Unlike devices and methods under the present state of the art, the invention does not require any direct mechanical connection to transfer the power from the drive source (e.g. an electric motor or similar) to the cutting element. The invention makes use of power transmission by means of a magnetic field and thereby generates fast mechanical vibration/rotational movements of the cutting element to perform the desired cut or perforation, for example to open up the lens capsule of an eye. The vibration or rotational frequency is preferably in the range here of above 30 Hz, more preferably above 50 Hz and more preferably still in the kHz or ultrasound range. The frequency here can be in an order of magnitude that is either considerably lower or higher than the elastic relaxation time (natural frequency) of the diaphragm or eye lens capsule, which produces a particularly reliable cutting effect or perforation, and even if the cutting edge of the moving cutting element has not been ground to optimum sharpness and/or in the event of a cutting element designed as a cutting ring not resting in a circular manner against the lens capsule. These properties, among others, allow the cutting element to be manufactured from metals or from plastic at least partially coated with ferromagnetically-excitable metal. The vibrations that the cutting element performs as a result of the magnetic field acting upon it can be oscillatory. The cutting element can equally be set in to a rotary or rotational movement and it is of course also possible to superimpose a rotation on an oscillation of the cutting ring in order to improve the cutting effect. The frequency of the rotational movement can vary from that of the vibration. The field generator comprises preferably at least two exciter magnets that generate a moving induced field, which can for example include or consist of electromagnets. Nor is it necessary for the cutting element to describe one complete revolution or event several revolutions in order to carry out the desired cut, but in the case of an appropriate design of the cutting element, for example as a cutting ring with a cutting edge extending around its entire circumference, a partial revolution through an angle of perhaps only a few degrees in order to open up the lens capsule.

In a first embodiment, the exciter magnets are arranged on an annular magnet holder which when in surrounds the head of the patient at a distance. In an another embodiment, the field generator or its exciter magnets are preferred to be capable of being positioned at or near the eye by having them incorporate a contact element, preferably annular or annular segments, positionable near or on the sclera and/or the cornea of the eye, with the exciter magnets arranged on the contact element. It is advisable for the cutting element to consist of a ferromagnetic material, in particular a metal, or to be provided with a ferromagnetic coating or a ferromagnetic core. Particularly in embodiments in which the cutting element is not guided by a mechanical holding element during the cutting process, a magnetic device that generates a magnetic field for holding and positioning field for the cutting element can be provided to hold the cutting element in the position desired by the surgeon. This magnetic device can consist e.g. in essence of at least one permanent magnet and/or one switchable electromagnet.

Thermal/electrical effects may be used to seal the edge of the cut after the mechanical cutting/perforation process, but not for the cutting process itself.

There is fundamentally no need for applying suction to the lens capsule or to the tissue to be cut.

The cutting element can in particular be designed as a continuous cutting ring, so that it forms a circumferential cut, or is designed similar to a hole saw with a serrated cutting edge. However, the cutting element can also be designed as a rotor with two or more vanes, the rotor vanes of which are fitted with sharp cutting edges at their outer radial ends. A two-vane rotor is especially preferred in this embodiment. It is advantageous if the rotor vanes are designed such that they can be introduced lengthwise into the eye through a small cut or hole, with their sharp cutting edges pointing towards the eye lens to be opened up. The cutting element can have a central shaft or hub by which it is mounted in a bearing on the holding element such that it can rotated at least moved to and fro. It describes a rapid mostly circular motion in the electromagnetic field, so that a round hole is created in the capsule.

It is particularly advantageous if the rotor vanes on the cutting element are designed with preferably clover-leaf shaped active surfaces made from soft magnetic material, in other words if the rotor vanes are not designed as rod- or needle-shaped but have a comparatively large surface area perpendicular to the direction of the magnetic field lines generated by the field generator in which the magnetic field is effective. This design is particularly advantageous if the cutting element is only acted upon by the stray field of the magnetic field. Due to the relatively large surface are of the rotor vanes, the field strength of the magnetic stray field is still reliably sufficient to set the rotor in motion by means of its ferromagnetic areas arranged at the rotor vanes, for example radially outwards.

The cutting element is preferably manufactured from elastic material or material combinations. This then allows the cutting element to be pressed or folded together or deformed in some other way, so that it can inserted into the eye through the very small incisions usual in ophthalmic surgery, for example by being injected into the interior of the eye through a fine tube. The materials used for cutting head or cutting element may also have shape memory effect properties. Rapidly-changing/expanding materials (e.g. Nitinol as described in WO 2012/082386 A1) are less suitable, since sudden movements in the anterior chamber of the eye can result in uncontrolled contact and possible injury to intraocular tissue. Metals or plastic-metal combinations that slowly return to their original shape after deformation due to compression are the most suitable above all. A temperature change may also be used, effected by the input of energy (mechanical, electrical, optical). Alternatively, it is possible to initiate a change of shape by mechanical, electrical and/or optical stimulation. The memory effect is particularly easy to achieved in the disposable version, as the cutting element only has to remember its shape once after a shape change, e.g. compression in an injector.

Alternatively or additionally, other mechanical elements, such as microsprings or elastic bridges, can effect a changed of shape of the cutting element inside the eye.

Optical elements can be mounted on the cutting head to allow the capsule cutter to be centered inside the eye, possibly in combination with a laser beam or light spots, operating microscope, computer-controlled video system. For example, the cutting element may be fitted with a central orifice opening, a lens or an optical gap which can be actuated with an optical centering device, preferably arranged on the field generator, such as a cross-hair, a laser target beam or a light beam to determine the position of, and/or to position, the cutting element.

The invention therefore creates a new device for perforating/cutting tissue, particularly in or at the eye. The device is generally used for anterior and posterior perforation (capsulotomy, rhexis) of the human eye lens. The device comprises a cutting element or cutting head that can be introduced into the eye through a small incision and has a device arranged outside the eye with which mechanical vibrations or movements are produced by electromechanical means, as if with a small electric motor, at the cutting element. The cutting element set into mechanical, mostly oscillating, vibrations in this way produces a cutting effect in the eye due to its direct contact with the tissue, without the cutting element having to be coupled mechanically to an external drive through the small incision in the eye, and in one preferred embodiment it is not even necessary for the cutting element to held from outside by a holder the cutting process. The opening of the eye lens capsule has a diameter in the range of a few tens of µm to a few millimeters (e.g. 0.01 mm to 10 mm).

If a cutting element with a continuous annular (linear) cutting edge is used, the design be such that the cutting ring vibrates mainly in the Z axis, i.e. in the direction of the lens capsule and back, in other words the field generator acts together with the cutting element as a kind of (oscillating) linear motor. Vibrations in an XN plane perpendicular to this can have a lesser cutting quality, depending on the design of the cutting element.

The preferred oscillatory vibration of the cutting head can be supported by a rotational motion. The electromagnetic field generated by the field generator can cause rotational movement of the cutting element or parts thereof. The rotational motion and oscillation in the circumferential or Z direction can also have different frequencies.

The frequency of the vibrations is however chosen so that a clean perforation of the lens capsule is obtained, which as a rule is ensured if the frequency is either substantially smaller or greater than the natural frequency of the tissue to be cut. Ideally, it lies in the range from a few Hz through the kHz range into the MHz range (ultrasound). The vibration of the cutting element or a cutting edge mounted on it is only necessary for a short time (<1 minute) to perform the necessary cut, The cutting element can be introduced into the eye through the normal incisions in an eye operation (cuts smaller than 2.8 mm). This is done using the injector or tube systems normal in ophthalmic surgery, through which artificial intraocular lenses, capsule clamping rings, vitreous body instruments and the line are introduced into the interior of the eye during eye operations. In this, the materials are compressed in the injector system and unfold or return to their original shape inside the eye. Materials with shape memory effect properties are particularly suitable for this. For the cutting head, these can be (metal-coated) plastics and metals with shape memory effect properties. The memory effect here can be e.g. initiated optically, by temperature-dependency or mechanically.

The cutting head or cutting element can be designed such that an optical element allows it and therefore the rhexis, to be centered relative to the optical axes (visual axis, cornea apex, pupil center, Purkinje reflex,). The cutting head or cutting element can include a central opening/lens/optical gap in the middle, for example. This can be controlled using an optical element (e.g. laser beam, light on the operating microscope). The surgeon can use his own eye for this, or the centered alignment can be controlled using electronic image processing.

These and other objects, aspects, features and advantages of the invention will become apparent to those skilled in the art upon a reading of the Detailed Description of the invention set forth below taken together with the drawings which will be described in the next section.

BRIEF DESCRIPTION OF THE DRAWINGS

The invention may take physical form in certain parts and arrangement of parts, a preferred embodiment of which will be described in detail and illustrated in the accompanying drawings which form a part hereof and wherein:

FIG. 5 is a side elevation of the subject of FIG. 4.

DESCRIPTION OF PREFERRED EMBODIMENTS

Figure 1:
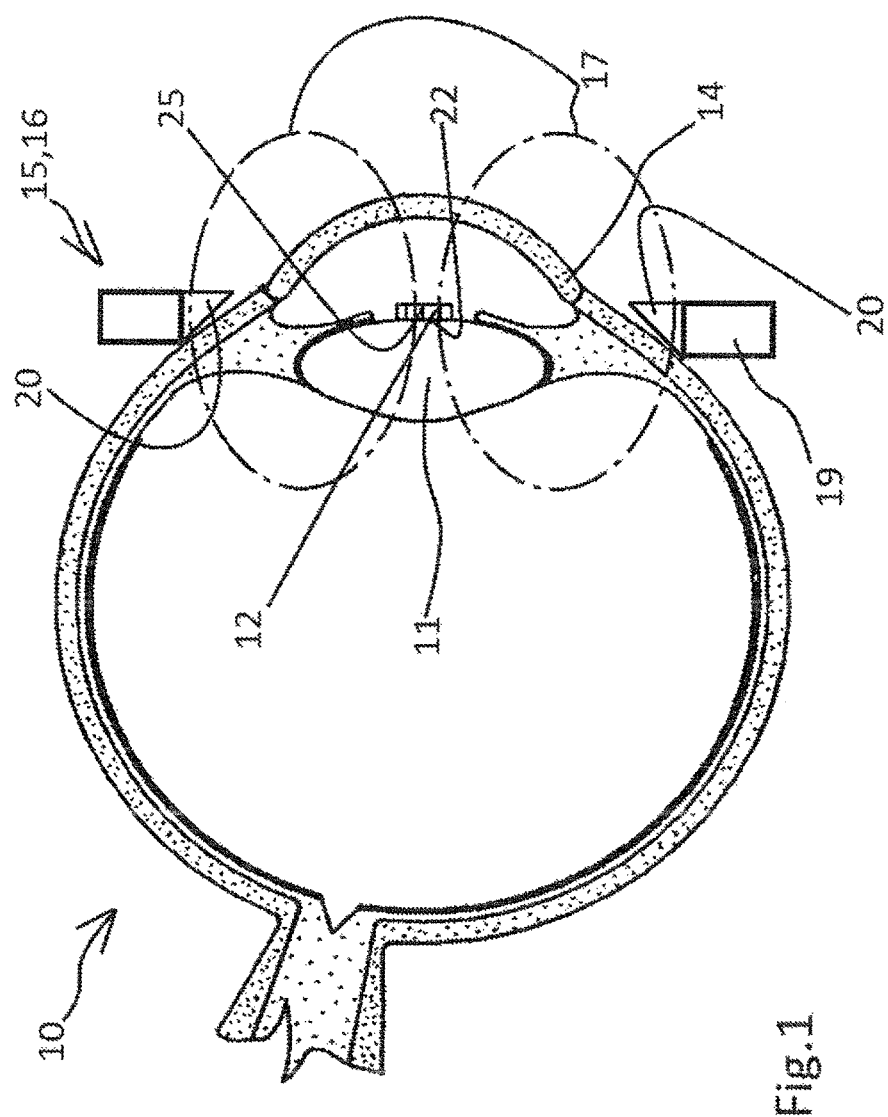
FIG. 1 is a schematic cross-sectional diagram of a first embodiment of a device according to the invention for performing a rhexis on the human eye.
Figure 2:
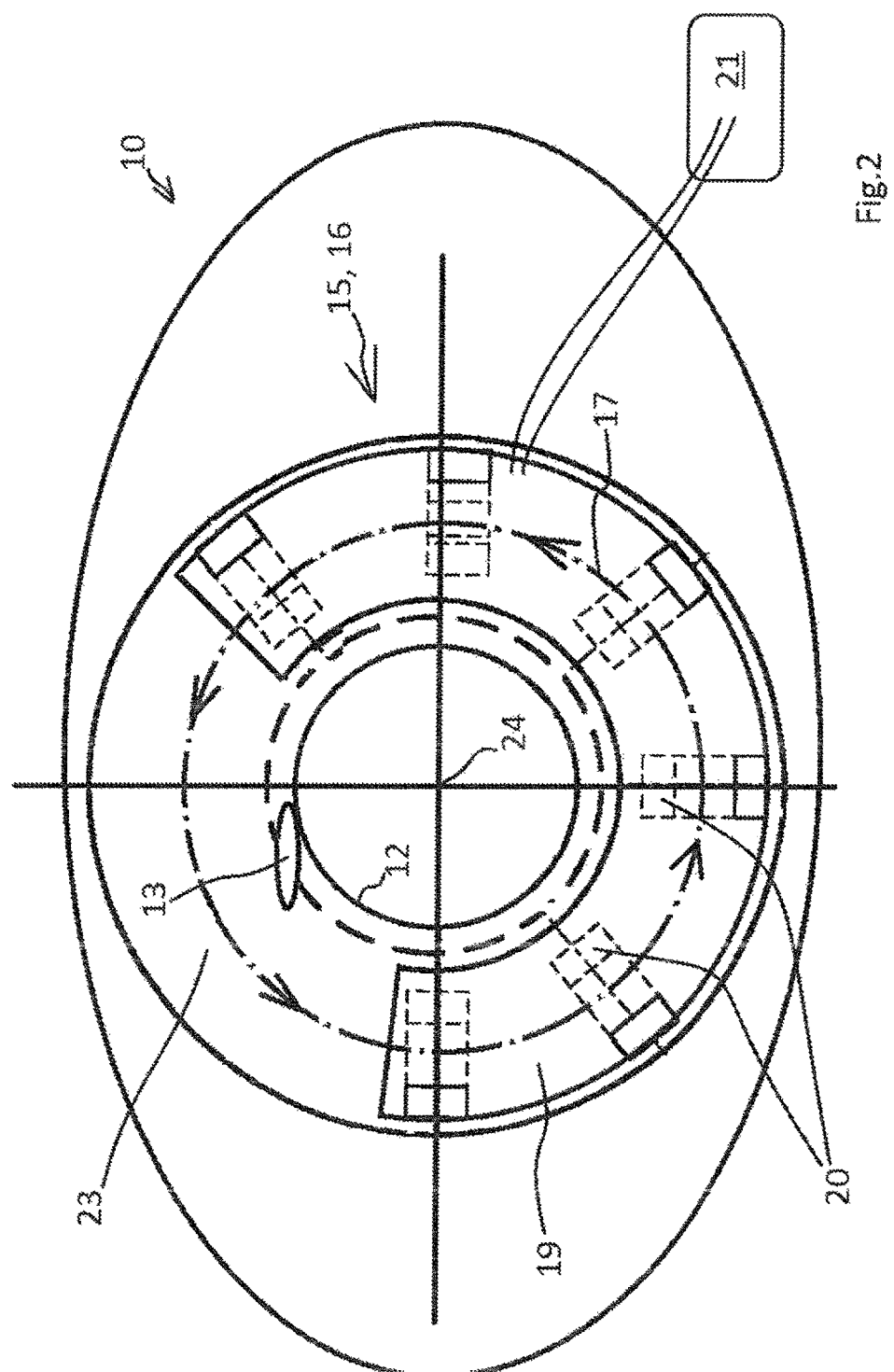
FIG. 2 is the subject of FIG. 1 in a plan view on the eye.

Referring now to the drawings wherein the showings are for the purpose of illustrating preferred and alternative embodiments of the invention only and not for the purpose of limiting the same, FIGS. 1 and 2 show a first embodiment of a device according to the invention used for producing a rhexis, in other words a circular cut in the eye 10 for opening the eye lens 11. The device includes here a cutting element 12, which by means of a small incision 13 in the cornea 14 of the eye 10 to be operated on can be introduced into the interior of the eye. The cutting element can be elastically deformable for this, so as to permit to be introduced, similar to an intraocular lens, into the interior of the eye through the comparatively small cut 13 using methods familiar to the eye surgeon. The cutting element is magnetisable or magnetic, for which purpose it is either completely made of metal with ferromagnetic properties, or has a metallic coating, a ferromagnetic core or a bracing made of (ferromagnetic) metal.

The device also includes a drive device 15 arranged outside the eye, the principal component of which is a field generator 16 for generating an induced electromagnetic field, shown diagrammatically in the drawings by a dotted dashed line 17. The induced electromagnetic field generated by field generator 16 acts on the cutting element 12 inserted into the interior of the eye by the latter by moving the latter to and fro axially in the Z axis 18 and/or rotationally around the Z axis, or setting into oscillating rotary motion.

In the embodiments shown in FIGS. 1 and 2, the field generator 16 has a number of exciter magnets 20 arranged in an annular segment contact element 19, these being electromagnets, which switched on an off for the generation of the induced field by a control unit 21 which is only shown schematically. The exciter magnets 20 are operated in such a way for this that they generate an induced field that moves along a circular path around the Z axis 18, on the basis of this the cutting element 12 inside the interior of the eye is set into a corresponding rotary motion. A generator field in the Z axis can be superimposed on the circular rotating induced field by switching on and off of the exciter magnets, preferably in a pulsating manner, as a result of which a force is exerted against the cutting element in an axial direction against the eye lens 11, against which the annular cutting element 12 presses with its front cutting edge.

It can be seen in FIG. 2 that the annular segment contact element 19, upon which the total of six exciter magnets are arranged in the embodiment, has a gap 23 extending around an angle of some 120°. In this area the contact element, which otherwise rests again the cornea of the eye, leaves a working area free for the surgeon where the latter can affect the incision 13, through which the cutting element can be introduced into the interior of the eye and then removed after the cut has been effected, and through which the cutting element can be correctly aligned with suitable tool before switching on the field generator. The incision 13 is also used later for inserting into the eye the artificial lens to be implanted.

To facilitate the correct alignment of the cutting element 12 in the eye, the device is equipped with a centering device arranged on the field generator 16, which in the first embodiment consists of two light beam projectors, which are not shown in any further detail, with which cross-hairs can be projected on to the cornea of the eye as shown by 24 in FIG. 2. The cutting element 12 has an optical centering device, comprising for example of a crossed consisting of two intersecting, preferably flexible braces or threads, the intersection of which can be brought by the surgeon to exactly under the intersection of the cross-hairs 14 in order to bring the cutting element 12 into exactly the desired position on the eye lens 11. It is possible to provide this centering element, shown in FIG. 1 as 25, in a ferromagnetic material, so that the said centering element performs the conversion of the electromagnetic field into the desired mechanical motion of the cutting element 12.

Figure 3:
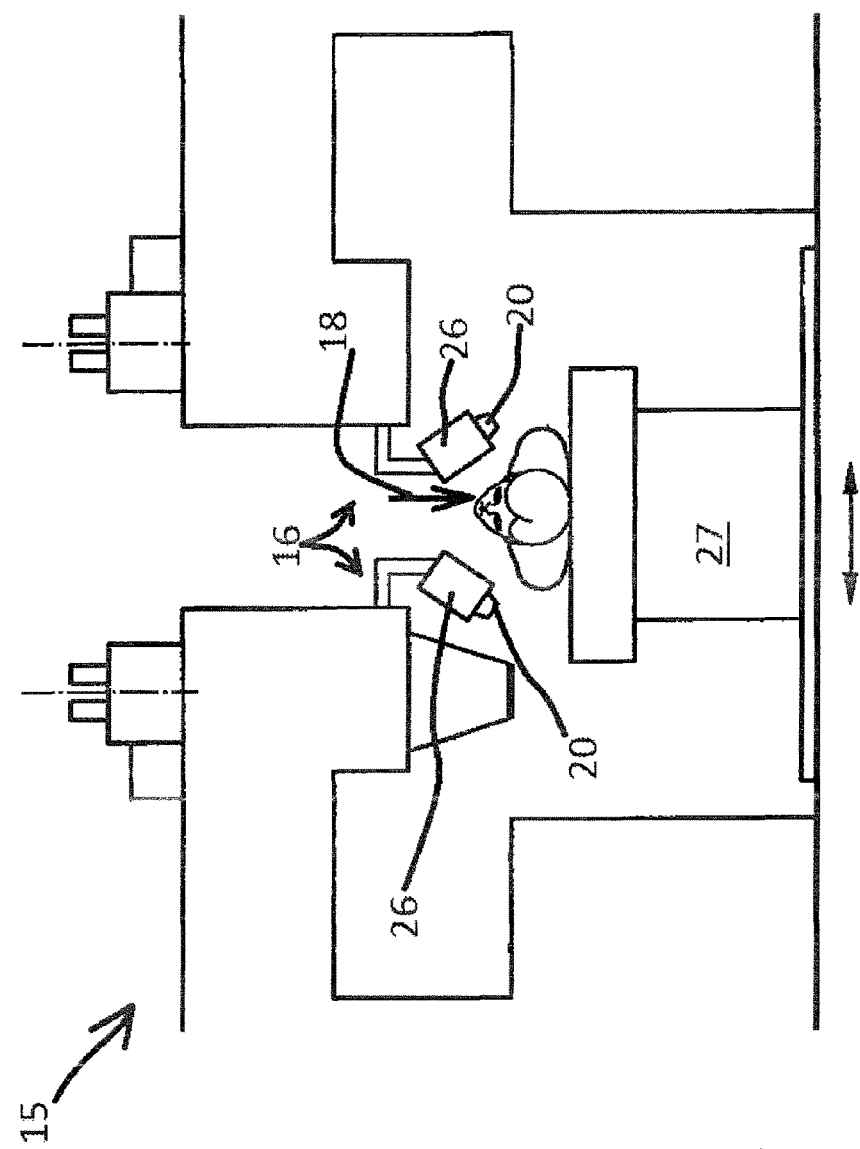
FIG. 3 is a simplified a second embodiment of the invention showing a head-on view of a patient being treated with the device.

The second embodiment illustrated in FIG. 3 differs from the embodiments in FIGS. 1 and 2 mainly in that the field generator for generating the electromagnetic field is not arranged here in the immediate vicinity of the cutting element directly at the eye of the patient to be operated upon, but on an item of equipment that surrounds the entire head of the patient at a greater distance from the cutting element. The exciter magnets here are arranged on magnet holders 26, of which there are several, preferably arranged at even angular distances, surrounding the head of patient at the height of eye to be operated upon. It can be seen in the embodiment shown in FIG. 3 that the operating table 27 with the patient lying on it can be moved sideways so as to adjust the eye to the optimal position relative to the magnet holders 26.

Figure 4:
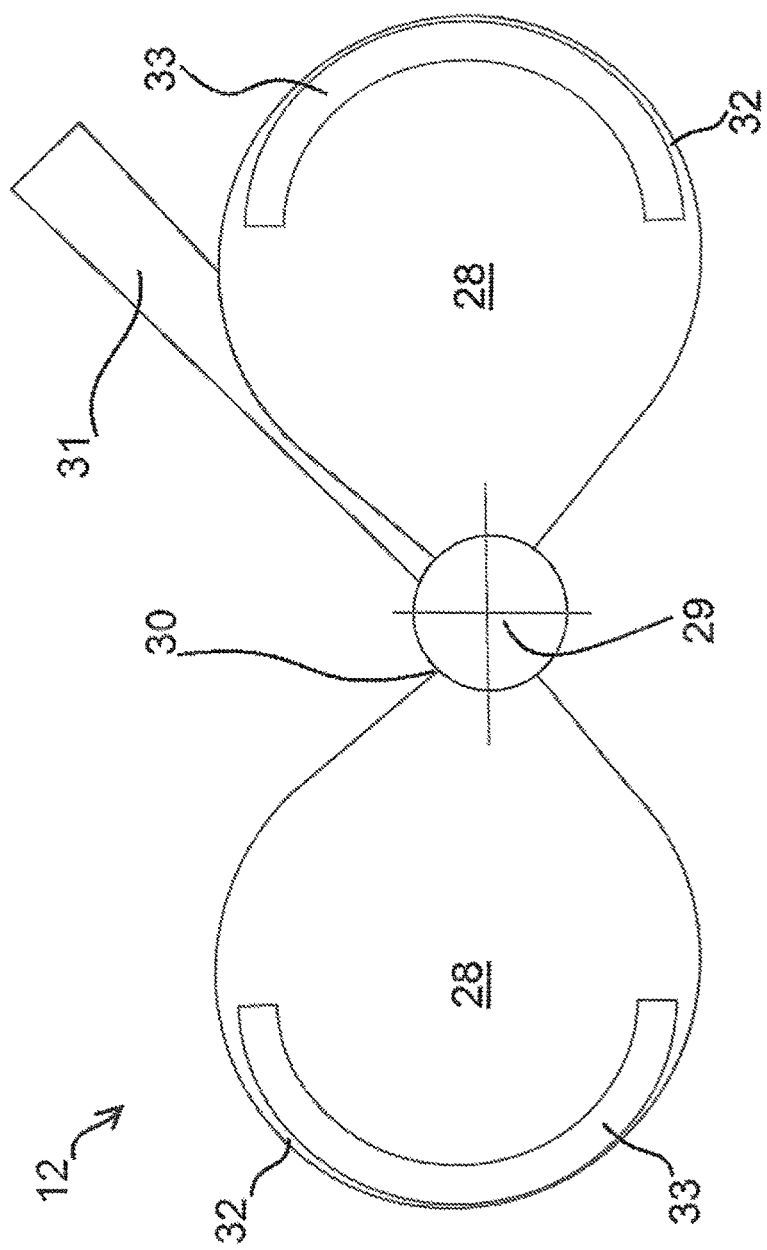
FIG. 4 is view from below a preferred embodiment of a cutting element used in the invention.

FIGS. 4 and 5 show and alternative design of a cutting element used in the invention. In this embodiment, the cutting element 12 has two cloverleaf-shaped rotary blades 28 arranged on a central shaft 29 of the cutting element designed as a two-vane rotor 30. The rotor shaft 29 is mounted such that it can rotate in a bearing in a holding element 31, with which the cutting element is introduced into the interior of the eye by the surgeon through the incision and can be held in the desired position. The rotor vanes, which comprise relatively large areas manufactured from soft magnetic material, can be elastically deformable for this, so that they can be folded and thereby made smaller for insertion of the element into the interior of the eye. The rotor vanes are fitted with cutting edges or tips 33 at their out radial areas 32, which create a circular opening in the eye lens in the desired manner when the cutting rotor rotates inside the eye. The compression forces acting in the axial direction (Z axis) can then be exerted by the surgeon or a surgical robot by means of the holding element.

The invention creates a contactless, magnetic quasi-electronic drive for moving the cutting element inside the interior of the eye, in which the cutting element corresponds to the moveable rotor and the field generator corresponds to the static stator. The invention allows the eye lens to be opened up with great precision for carrying out a capsulotomy by reliably avoiding external influences during the actual cutting process that occurred with previous systems as a result of the cutting element being mechanically coupled to the associated drive.

In order to insert the cutting element easily into the interior of the eye through the small cut 13 in the cornea and to remove it in the same way, the cutting element is preferably deformable and is made in particular of a shape-memory material, as is known in many areas of technology. Such shape-memory methods can be plastic or metallic materials which return to their original shape after being subjected to light or heat energy, for example.

While considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. A device for producing cuts or perforations on a human or animal eye at the anterior or posterior opening of the eye lens (capsulatomy, rhexis), the device comprising a cutting element that can be inserted into an associated interior of an associated eye and a drive device which is arranged outside of the associated eye in order to cause movement, in articular oscillatory vibrations or rotation of the cutting element inside the associated interior of the associated eye, the drive device having a field generator for generating a magnetic or electromagnetic excitation field and the cutting element can be excited, in particular driven, by way of the field generated by the field generator, the cutting element is formed as a continuous cutting ring.

2. A device for producing cuts or perforations on a human or animal eye at the anterior or posterior opening of the eye lens (capsulatomy, rhexis), the device comprising a cutting element that can be inserted into an associated interior of an associated eye and a drive device which is arranged outside of the associated eye in order to cause movement, in particular oscillatory vibrations or rotation of the cutting element inside the associated interior of the associated eye, the drive device having a field generator for generating a magnetic or electromagnetic excitation field and the cutting element can be excited, in particular driven, by way of the field generated by the field generator, the cutting element is formed as a multi-vane rotor having a plurality of vanes, the plurality of vanes being fitted with sharp cutting edges at their outer radial ends.

3. The device according to claim 2, wherein the multi-vane rotor is a twin-vane rotor.

4. A device for producing cuts or perforations on a human or animal eye at the anterior or posterior opening of the eye lens (capsulatomy, rhexis), the device comprising a cutting element that can be inserted into an associated interior of an associated eye and a drive device which is arranged outside of the associated eye in order to cause movement, in particular oscillatory vibrations or rotation of the cutting element inside the associated interior of the associated eye, the drive device having a field generator for generating a magnetic or electromagnetic excitation field and the cutting element can be excited, in particular driven by way of the field generated by the field generator, the cutting element is fitted with an optical centering element which can be actuated with an optical centering device.

5. The device according to claim 4, wherein the optical centering element includes at least one of an orifice, a lens and an optical gap, the optical centering device being arranged on the field generator and including at least one of a cross-hair, a laser target beam and a light beam to determine the position of, and/or to position, the cutting element.

* * * * *